United States Patent
Bechhoefer

(10) Patent No.: US 8,355,879 B2
(45) Date of Patent: Jan. 15, 2013

(54) TRENDING OF VIBRATION DATA TAKING INTO ACCOUNT TORQUE EFFECT

(75) Inventor: Eric Robert Bechhoefer, New Haven, VT (US)

(73) Assignee: Simmonds Precision Products, Inc., Vergennes, VT (US)

( * ) Notice: Subject to any disclaimer, the term of this patent is extended or adjusted under 35 U.S.C. 154(b) by 271 days.

(21) Appl. No.: 12/655,720

(22) Filed: Jan. 6, 2010

(65) Prior Publication Data

US 2011/0166799 A1    Jul. 7, 2011

(51) Int. Cl.
*G01B 5/28* (2006.01)
(52) U.S. Cl. .............................. 702/35; 702/56; 73/1.09
(58) Field of Classification Search .............. 702/33–35; 73/1.09
See application file for complete search history.

(56) References Cited

U.S. PATENT DOCUMENTS

| | | | |
|---|---|---|---|
| 4,766,967 A | 8/1988 | Slicker et al. | |
| 5,489,984 A | 2/1996 | Hariharan et al. | |
| 6,384,563 B1 | 5/2002 | Someya | |
| 6,567,757 B2 | 5/2003 | Bechhoefer et al. | |
| 6,574,572 B2 | 6/2003 | Bechhoefer | |
| 6,651,012 B1 | 11/2003 | Bechhoefer | |
| 6,711,523 B2 | 3/2004 | Bechhoefer et al. | |
| 6,728,658 B1 | 4/2004 | Bechhoefer | |
| 6,754,569 B2 | 6/2004 | Bechhoefer | |
| 6,847,917 B2 | 1/2005 | Bechhoefer | |
| 6,871,133 B2 | 3/2005 | Togai et al. | |
| 6,950,763 B1 | 9/2005 | Bechhoefer | |
| 7,031,820 B2 | 4/2006 | Ueda et al. | |
| 7,136,794 B1 | 11/2006 | Bechhoefer | |
| 7,272,513 B2 | 9/2007 | Bechhoefer | |
| 7,512,463 B1 | 3/2009 | Bechhoefer | |
| 7,882,394 B2 * | 2/2011 | Hosek et al. | 714/26 |
| 2006/0083617 A1 * | 4/2006 | Jolly et al. | 416/133 |
| 2007/0067678 A1 * | 3/2007 | Hosek et al. | 714/25 |

OTHER PUBLICATIONS

Eric Bechhoefer, Goodrich SIS, "A Method for Generalized Prognostics of a Component Using Paris Law", Apr. 29-May 1, 2008, 10 Pages.

* cited by examiner

*Primary Examiner* — Sujoy Kundu
(74) *Attorney, Agent, or Firm* — Muirhead and Saturnelli, LLC

(57) ABSTRACT

In vibration based mechanical diagnostics, algorithms may extract some feature of a component which may be used as a statistic of the components' health. A measured condition indicator corresponding to the analysis of the components' health may be a function of transmission error (TE). Because there exists a relationship between TE and the CI for a component that is faulted, the CI is correlated with power transmitted. In drive train components, power may be proportional to measured torque. In terms of diagnostics or trending of a component, it is desirable to reduce the scatter in the measured CI and account for this torque. The relationship between measured CI and torque may be captured over time. An increase in the correlation of torque with the CI would indicate an increase of TE which indicates the propagation of a fault.

17 Claims, 12 Drawing Sheets

TRENDING OF VIBRATION DATA TAKING INTO ACCOUNT TORQUE EFFECT

TECHNICAL FIELD

This application relates to the field of vibration analysis and, more particularly, to performing vibration analysis for the purpose of component monitoring.

BACKGROUND OF THE INVENTION

The transmission of power to rotors which propel helicopters and other shafts that propel devices within the aircraft induce vibrations in the supporting structure. The vibrations occur at frequencies that correspond to the shaft rotation rate, mesh rate, bearing passing frequency, and harmonics thereof. The vibration is associated with transmission error (TE). Increased levels of TE are associated with transmission failure. Similar types of vibrations are produced by transmissions in fixed installations as well. For various examples of systems and techniques using analysis of vibrations in connection with analyzing and/or adjusting rotating components of helicopters or other aircraft, see U.S. Pat. No. 6,567,757 to Bechhoefer et al., entitled "Reducing Vibration Using QR Decomposition and Unconstrained Optimization," U.S. Pat. No. 6,574,572 to Bechhoefer, entitled "Reducing Vibration Using QR Decomposition and Constrained Optimization," U.S. Pat. Nos. 6,950,763 and 7,272,513, both to Bechhoefer and entitled "Optimal Shaft Balance Using Integer Programming to Handle Discrete Adjustment," and U.S. Pat. No. 7,512,463 to Bechhoefer, entitled "Reducing Vibration Using QR Decomposition and Unconstrained Optimization for a Multi-rotor Aircraft", which are all hereby incorporated by reference.

Parts and components, such as those that may be included in a helicopter transmission, may be replaced in accordance with a predetermined maintenance and parts replacement schedule. These schedules provide for replacement of parts prior to failure. The replacement schedules may indicate replacement time intervals that are too aggressive resulting in needless replacement of working parts. This may result in incurring unnecessary costs as airplane parts are expensive. Additionally, new equipment may have installed faulty or defective parts that may fail prematurely.

Accordingly, it would be desirable to provide systems and techniques to efficiently detect part and component degradation and provide problem determination prior to failure and without relying on schedule-based maintenance.

SUMMARY OF THE INVENTION

According to the system described herein, a method of indicating a propagating fault in a component includes measuring data corresponding to a condition indicator of the component and to an input factor. A relationship is determined between the condition indicator and the input factor. An effect of the input factor on the condition indicator is determined. A filtered condition indicator is determined based on the effect of the input factor on the condition indicator. The method further includes determining whether a propagating fault is indicated based on a correlation over time of the filtered condition indicator with the input factor. The input factor may be torque. Determining the effect of the input factor on the condition indicator may include using a state observer, such as a Kalman filter, a recursive least squares estimation, and/or a Particle filter. The component may be a rotating shaft. Data of the filtered condition indicator may have a reduced variance compared to the data measured corresponding to the condition indicator. The propagating fault may be determined based on a positive correlation over time between the filtered condition indicator and the input factor.

According further to the system described herein, a computer readable storage medium stores computer software that determines indication of a propagating fault in a component. The computer software includes executable code that measures data corresponding to a condition indicator of the component and to an input factor. Executable code may be provided that determines a relationship between the condition indicator and the input factor. Executable code may be provided that determines an effect of the input factor on the condition indicator. Executable code may be provided that determines a filtered condition indicator based on the effect of the input factor on the condition indicator. Executable code may be provided that determines whether a propagating fault is indicated based on a correlation over time of the filtered condition indicator with the input factor. The input factor may be torque. The executable code that determines the effect of the input factor may include executable code that uses a state observer, such as a Kalman filter, a recursive least squares estimation and/or a Particle filter. The component may be a rotating shaft. Data of the filtered condition indicator may have a reduced variance compared to the data measured corresponding to the condition indicator. The propagating fault may be determined based on a positive correlation over time between the filtered condition indicator and the input factor.

According further to the system described herein, a system for indicating a propagating fault in a component includes a first sensor that measures data corresponding to a condition indicator of the component and a second sensor that measures data corresponding to an input factor. At least one processor may process the data measured from the first sensor and the second sensor, the processor executing computer software stored on a computer readable storage medium. The computer software may include executable code that determines a relationship between the condition indicator and the input factor. Executable code may be provided that determines an effect of the input factor on the condition indicator. Executable code may be provided that determines a filtered condition indicator based on the effect of the input factor on the condition indicator. Executable code may be provided that determines whether a propagating fault is indicated based on a correlation over time of the filtered condition indicator with the input factor. The input factor may be torque. The executable code that determines the effect of the input factor may include executable code that uses a state observer, such as a Kalman filter, a recursive least squares estimation and/or a Particle filter. The executable code that determines the effect of the input factor may include executable code that uses a recursive least squares estimation. Data of the filtered condition indicator may have a reduced variance compared to the data measured corresponding to the condition indicator. The propagating fault may be determined based on a positive correlation over time between the filtered condition indicator and the input factor.

BRIEF DESCRIPTION OF DRAWINGS

Embodiments of the system described herein are explained in detail below on the basis of the figures which are briefly described as follows.

DETAILED DESCRIPTION OF VARIOUS EMBODIMENTS

Figure 1:
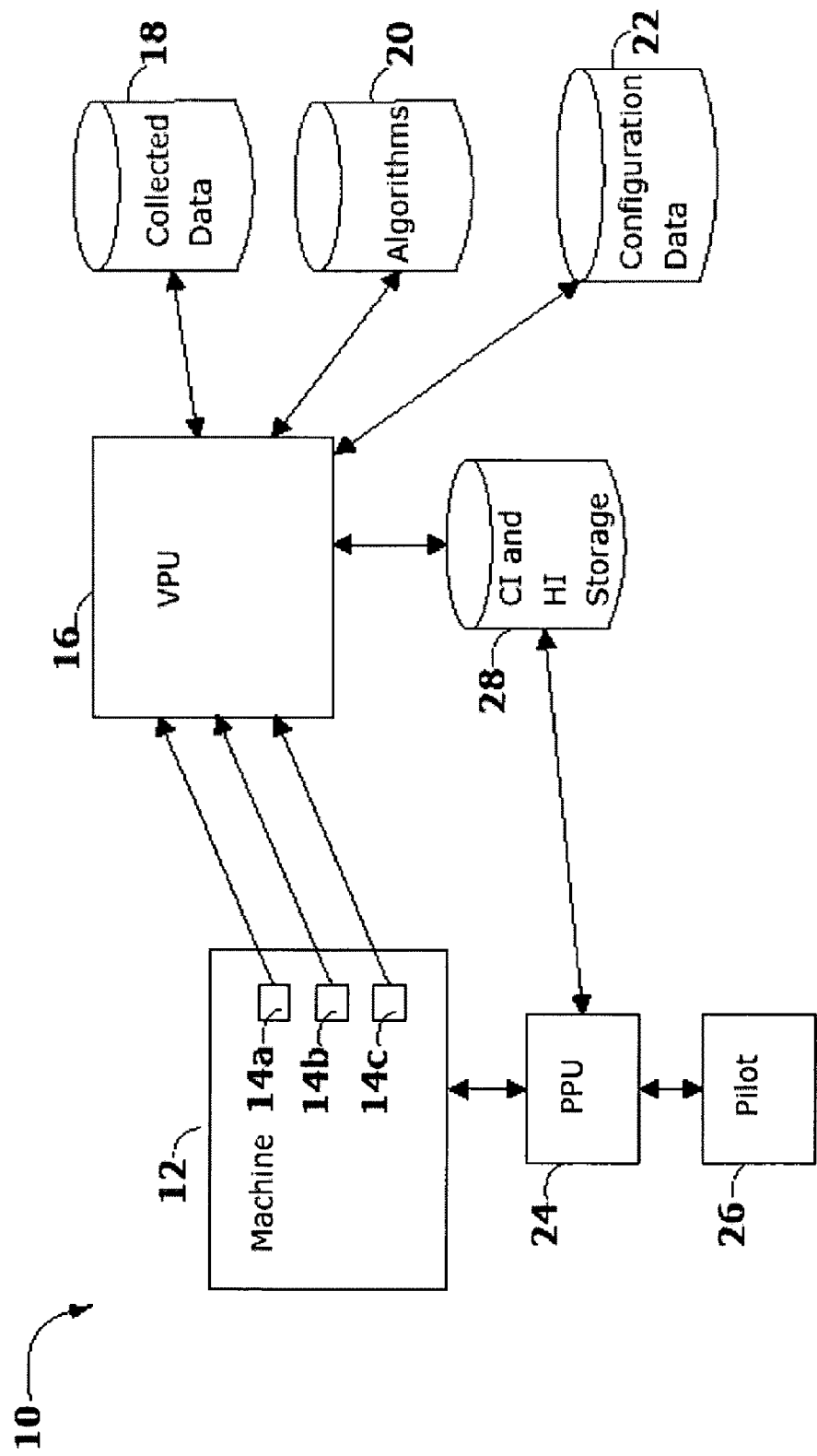
FIG. 1 is an example of an embodiment of a system that may be used in performing vibration analysis and performing associated monitoring functions.

FIG. 1 is a schematic diagram 10 showing an example of an embodiment of the system described herein that may be used in performing vibration analysis and monitoring of a machine 12, such as a portion of an aircraft. The machine 12 being monitored may be a particular component within an aircraft. A plurality of sensors 14a-14c may be located on the machine to gather data from one or more components of the machine. Data may be collected by the sensors 14a-14c and sent to a processor or a VPU 16 for data gathering and analysis. The VPU 16 analyzes and gathers the data from the sensors 14a-14c.

The VPU 16 may also use other data in performing analysis. For example, the VPU 16 may use additional collected data 18. One or more of a plurality of algorithms 20 may be used as input into the VPU 16 in connection with analyzing data that is gathered from the sensors 14a-14c. Additionally, configuration data 22 may be used by the VPU 16 in connection with performing an analysis of the data received, for example, from the sensors 14a-14c. Generally, the configuration data 22 may include parameters and the like that may be stored in a file. The collected data 18, the algorithms 20, and the configuration data 22 are described in more detail elsewhere herein.

The VPU 16 may receive input from the collected data 18, one or more of the algorithms 20, and the configuration data 22 to determine one or more condition indicators (CIs). In turn, the CIs may be used to determine health indicators (HIs) that may be stored, for example, in a CI and HI storage 28. CIs describe aspects of a particular component that may be useful in making a determination about the state or health of a component, as further discussed elsewhere herein. Generally, CIs and HIs may be used in connection with different techniques in determining an indication about monitored components such as the machine 12. The configuration data 22 may include values for parameters that may vary in accordance with the type of the component being monitored.

It should be noted that the collected data 18 may include data collected over a period of time from the sensors 14a-14c mounted on the machine 12. A user, such as a pilot 26, may connect a special service processor, such as a primary processing unit (PPU) 24, to the machine 12 to obtain different types of data such as CI and HI values.

Generally, different types of data gathering equipment used herein, such as the sensors 14a-14c, may be any suitable type of sensor, tachometers and/or accelerometer and/or high resolution accelerometers and index sensors (indexors). The sensors 14a-14c may be mounted on a component of the machine 12 at carefully selected locations throughout an aircraft. Accelerometers may provide instantaneous acceleration data along whatever axis on which they are mounted of a particular device. Accelerometers may be used in gathering vibration analysis data and accordingly may be positioned to optimally monitor vibration generated by one or more mechanical components such as gears, shafts, bearings or planetary systems. Each component being monitored may generally be monitored using two independent sensors to provide confirmation of component faults and to enable detection of sensor faults. Data from the sensors 14a-14c may be sampled at high rates, for example, up to 100 kilohertz, in order for the VPU 16 to produce the necessary CI and HI indicators. Data from the sensors 14a-14c may be acquired synchronously at precise intervals for measuring vibration and rotational speeds.

No accelerometer is completely isolated from any other component. Thus, the component rotational frequencies may share as few common divisors as possible in order to maximize the effectiveness of the monitoring function being performed. For example, all gears being monitored may have differing number of teeth and all bearings may have differing numbers and sizes of balls or rollers. This may allow individual components to be spectrally isolated from each other to the extent that their rotational frequencies are unique.

The sensors 14a-14c may be used as indexers to monitoring and gather data about a particular component of the machine 12. The indexers may produce a periodic analog signal whose frequency is an integer multiple of the instantaneous rotation frequency of the shaft that they are monitoring. These signals may be generated magnetically using one or more evenly spaced metallic protrusions on the shaft passing by the fixed sensor. Alternatively, these may be monitored optically using a piece of optically reflective material affixed to the shaft. It should be noted that each index point may be fixed in time as precisely as possible. In connection with magnetic sensors, this may be accomplished, for example, by interpolating the zero crossing times of each index pulse and similarly for optical sensors by locating either rising or falling edges. Assuming the minimal play or strain in the drive train when something is under load, the relative position and rate of any component may be calculated using a single index or wave form. In accordance with the system described herein, the sensors 14a-14c may measure data corresponding to the CI and to an input factor, such as torque, as further discussed elsewhere herein.

It should be noted that the VPU 16 is intended to be used in a wide variety of mechanical and electrical environments. As described herein, different components of an aircraft may be monitored. However, this is only one example of a type of environment in which the system described herein may be used. As known to those skilled in the art, the general principles and techniques described herein have much broader and general applicability beyond a specific aircraft environment that may used in an example here. It should also be noted that in a particular embodiment, each mechanical part being monitored may have one or more sensors associated with it where a sensor may include, for example, an accelerometer or a tachometer. Generally, accelerometers may be used, for example, to obtain data regarding vibrations and a tachometer may be used, for example, to gain information and data regarding rotation or speed of a particular object. Data may be obtained and converted from the time domain to the frequency domain.

A particular algorithm may provide one or more CIs. Each of the algorithms may produce or be associated with a particular CI. One or more CIs may be used in combination with one or more functions to produce an HI for a particular part or type. Each of the algorithms may be associated or classified with a particular part or type. The CI generally measures vibrations and applies a function as described in accordance for each algorithm. Generally, vibration is a function of the rotational frequency and the amount of torque. Using torque and a particular frequency, a CI may appropriately be determined in accordance with a selected algorithm for a part. For example, the algorithms 20 may be classified into four families or groups in accordance with the different types of parts. Families of algorithms may include shaft, gears, bearings, and planetary gears. Associated with each particular part being monitored may be a number of CIs. Each CI may be the result or output of applying a different one of the algorithms for a particular family. For example, in one embodiment, each gear may have an associated twenty seven CIs, each bearing may have nineteen CIs, each shaft may have twenty two CIs, and each planetary gear may have two or three CIs. It should be noted that each one of these numbers represents in this example a maximum number of CIs that may be used or associated with a particular type in accordance with the number of algorithms associated with a particular class or family. Generally, a different number of CIs that may be associated with a particular type such as a gear to take into account the many different ways in which a particular gear may fail. Thus, a CI may reflect a particular aspect or characteristic about a gear with regard to how it may fail. The VPU 16 may use the CIs as input along with portions of the data in connection with processing an algorithm to provide HIs and to determine and predict health of a component, such as the machine 12.

As mentioned above, HIs may be derived using one or more of the CIs. In calculating CIs, data acquisitions may occur by recording observed data values using the sensors 14a-14c that monitor different components. There may be a need for estimating data used in connection with CI calculations, for example, in instances in which there may be too little or no observed empirical data. For example, in connection with a power train, there may be a need to obtain estimated data, for example, for each bearing, shaft and gear within the power train to calculate CIs. However, insufficient empirical data may exist in connection with gear or bearing related measurements, such as, for example, those in connection with a gear or bearing fault due to the rare occurrence of such events. In such instances, mean and threshold values may be derived using other techniques.

For further discussion of determining CIs and HIs, and uses thereof in determining and predicting the health of a component in vibration-based diagnostic systems, see U.S. Pat. No. 6,651,012 to Bechhoefer, entitled "Method and Apparatus for Trending and Predicting the Health of a Component," U.S. Pat. No. 6,711,523 to Bechhoefer, entitled "Method and Apparatus for Determining a Condition Indicator for Use in Evaluating the Health of a Component," U.S. Pat. No. 6,728,658 to Bechhoefer, entitled "Method and Apparatus for Determining the Health of a Component Using Condition Indicators," U.S. Pat. No. 6,754,569 to Bechhoefer, entitled "Method and Apparatus for Normalizing Condition Indicators," U.S. Pat. No. 6,847,917 to Bechhoefer, entitled "Method and Apparatus for Selecting Condition Indicators in Determining the Health of a Component," and U.S. Pat. No. 7,136,794 to Bechhoefer, entitled "Method and Apparatus for Estimating Values for Condition Indicators," which are all hereby incorporated by reference.

Figure 2:
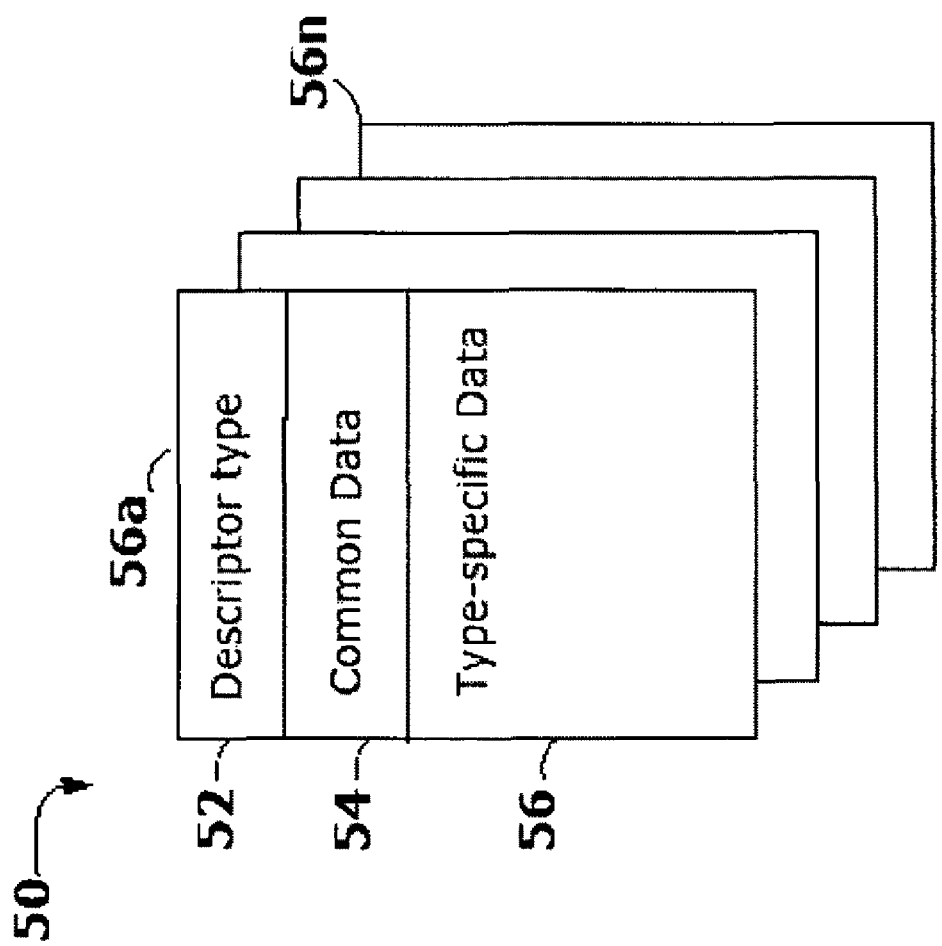
FIG. 2 is an example representation of a data structure that includes aircraft mechanical data.

FIG. 2 is a schematic illustration of an example of a data structure 50 that includes aircraft mechanical data. The data structure 50 includes one or more descriptors 56a-56n. In an embodiment, there may be one descriptor for each sensor. A descriptor associated with a particular sensor may include parameters relevant to the particular component being monitored. Each of the descriptors may include three portions of data: a field 52 that identifies a particular type of descriptor, a common data portion 54 containing data fields common to all descriptor types, and a type specific data portion 56 which includes different data fields that may vary in accordance with the descriptor type 52.

Descriptor types may include, for example, an indexer, an accelerometer, a shaft, a gear, a planetary gear, or a bearing descriptor type value corresponding to each of the different types of descriptors. The common data portion 54 may include, for example, a name, part number and identifier. The identifier in the common data field 54 may uniquely identify the component and type.

The data structures described in connection with FIG. 2 are those that may be used in connection with storing data obtained and gathered by a sensor when monitoring a particular component of the machine 12. Data may be gathered and stored in the data structure for a particular descriptor or descriptors and sent to the VPU 16 for processing. It should be noted that a particular set of data may be gathered at a particular instance and time, for example, in connection with the synchronous data gathering described elsewhere herein. In connection with this, a data set that includes multiple descriptors from sampling data at a particular point in time may be sent to the VPU 16. Data structures may be associated with an analysis definition that provides for specific data acquisition and subsequent processing of data to produce a set of indicators for each of the desired components.

The hardware and/or software included in any of the embodiments noted herein may provide for data acquisition and/or computations that may be performed by one or more digital signal processors (DSPs) running at a particular clock speed, such as 40 MHz, having a predetermined numerical precision, such as 32 bits. The processors may have access to shared memory. In one embodiment, sensors may be multiplexed and data may be acquired in groups, such as groups of eight. Other embodiments may vary the number in each group for data sampling. The sampling rates and durations within an acquisition group may also vary in an embodiment. Data may be placed in the memory accessed by the DSPs on acquisition. In one embodiment, the software may be a combination of ADA95 and machine code. Processors may include the VPU 16 as described herein as well as a DSP chip.

Figure 3:
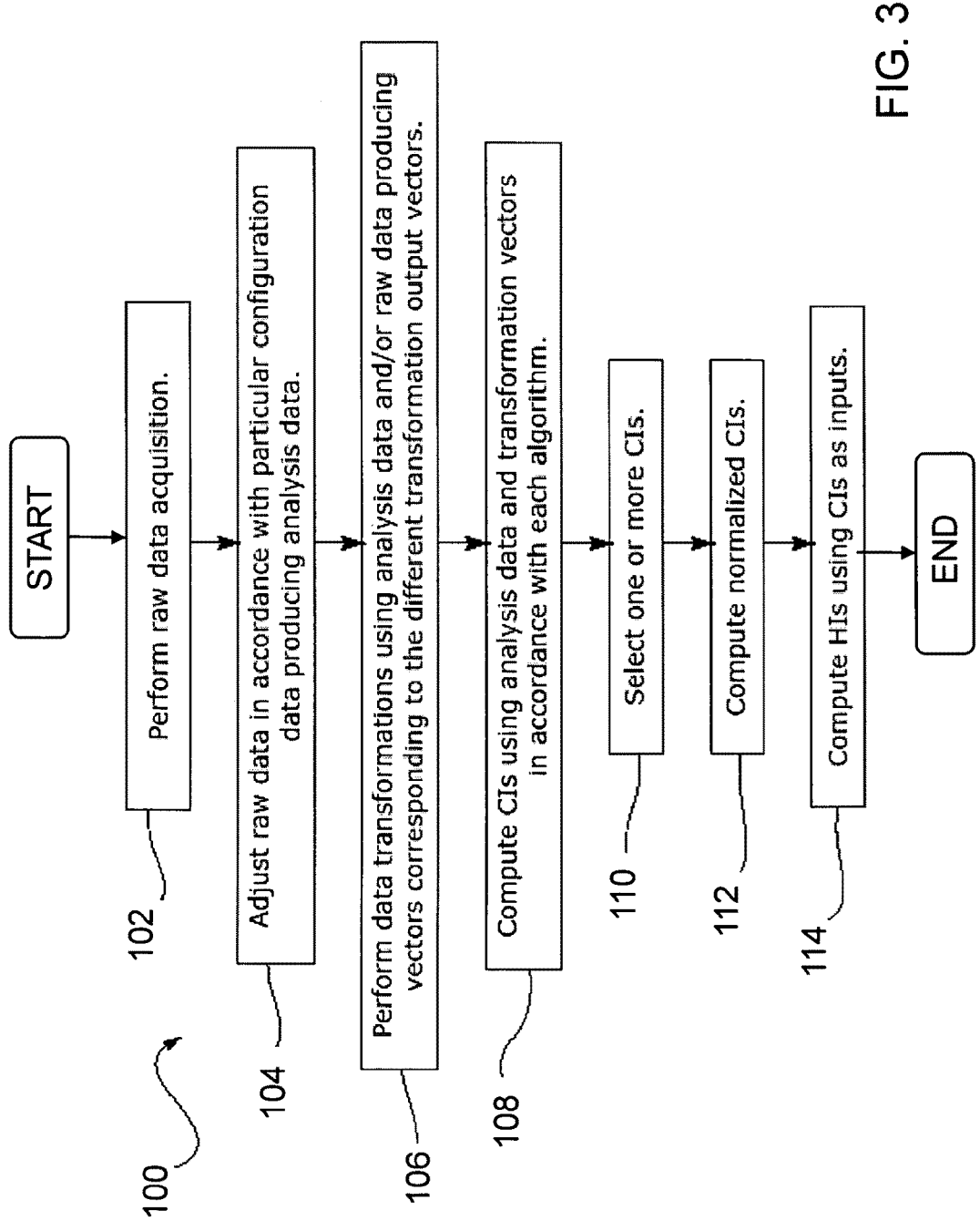
FIG. 3 is a flow chart showing steps of an embodiment for determining condition indicators (CI) and health indicators (HIs) for use according to the system described herein.

FIG. 3 is a flow chart 100 showing steps for determining the health of a part as indicated by an HI according to an embodiment of the system described herein. At step 102, raw data acquisition is performed. This may include, for example, issuing appropriate commands causing the VPU 16 to perform a data acquisition. After the step 102, processing proceeds to a step 104 where the raw data may be adjusted, for example, in accordance with particular configuration information producing analysis data as output. At the step 104, an embodiment may, for example, make adjustments to a raw data item acquired as may be related to the particular arrangement of components. Following the step 104, processing proceeds to a step 106 where data transformations may be performed using the analysis data and other data, such as raw data. The output of the data transformations includes transformation output vectors.

After the step 106, processing proceeds to a step 108 where CIs may be computed using the analysis data and transformation vector data as may be specified in accordance with each algorithm. After the step 108, processing proceeds to a step 110 where one or more CIs may be selected. Particular techniques that may be included in connection with the system described herein for selecting particular CIs are described elsewhere herein in more detail. After the step 110, processing proceeds to a step 112 where CIs may be normalized. After the step 112, processing proceeds to a step 114 where the selected and normalized CIs are used in determining HIs (see, e.g., U.S. Pat. No. 6,754,569, as noted above).

Note that techniques for determining an HI may use normalized or other than normalized CI values as inputs, and accordingly, the step 112 may be optional. For example, techniques for determining an HI that use normalized CI values as inputs may include the non-linear map technique and the hypothesis test method of HI generation. Techniques for HI determination that use CI values other than normalized CI values may include multiple torque bands with one for each CI or group of CIs belonging to different torque bands. In an embodiment, HI computations may not be executed in real time due to the lengthy processing times in executing the different algorithms described herein. Rather, they may be performed, for example, when a command or request is issued, such as from a pilot, at predetermined time intervals, and/or when a given flight regime is detected. After the step 114, processing is complete.

For any generic type of analysis (e.g., gear, bearing, and/or shaft), a subset of the diagnostics indicators or CIs may be selected. The CIs which are best suited to specify the fault indication may be developed over time through data analysis. Faults may be calculated at the component level and an HI may be calculated for a given component. If there is a component fault, then there may be a sub-assembly fault, and therefore a drive train fault. It should also be noted that operating characteristics of a system may define the probability of a false alarm (PFA) and the probability of detection (PD). False alarm rate and detection rate are two factors that may affect selection of particular values, such as thresholds within a particular system. For example, false alarm rate may be a determining factor because of the high cost associated with false alarms and the fact that they may corrode confidence when a real fault is detected. It should be noted that other embodiments and other applications may have different considerations. For example, an acceptable false alarm rate, such as 1 false alarm per 100 flight hours, may be established. An estimate of the number of collection opportunities per flight hours may be determined, such as four data collections. A number of HIs may be selected for the system, such as approximately 800. A confidence level may be selected, such as that there is a 90% probability that a false alarm rate is less than 1 per 100 flight hours.

Analyzing various CI's may require that a distribution be assumed in connection with a health analysis of a component. Distributions may be assumed to be normal (Gaussian) and/or may be other than Gaussian, such as assuming a Rayleigh distribution, as further discussed elsewhere herein. Ideally, an analysis tool would provide a predictor for component failure analysis such that component failures are always detected while the number of false positives (incorrect indicators that a component has failed) is minimized or even zero. Knowledge of the distribution of values for a particular CI calculation when the corresponding component is healthy (healthy component distribution) allows for calculation of the expected number of false positives given a particular threshold setting for the CI value.

Furthermore, it may also be beneficial to perform component analysis using a different distribution of data corresponding to data that is expected in connection with component failure (i.e., a failed component distribution). In such a case, when the data exceeds the first threshold set according the healthy component distribution, then the component may be further tested according to the failed component distribution. In some embodiments, a component may be deemed failed simply by exceeding the healthy component distribution while in other embodiments, a component may not be deemed failed unless the corresponding measured data first exceeds a threshold set according to the healthy component distribution and then the data also indicates failure based on the failed component distribution. In some cases, use of the failed component distribution may facilitate a measure of how much the component has failed (i.e., the urgency of component repair/replacement).

In an embodiment herein, it is assumed that the distribution of the magnitude vibration energy is the Rayleigh distribution for healthy components. Thus, a model for the magnitude of shaft vibrations when the shaft and related components are healthy may use the Rayleigh distribution. Threshold setting procedures may be provided using the Rayleigh distribution in connection with anomaly detection (e.g. component is no longer normal) and failure detection (component is damaged). Using a mathematical function that most accurately reflects the actual distribution of the vibration data under normal conditions for a healthy component allows for more precise calculation of the expected false alarm rate. Setting thresholds using the health component distribution is useful for a number of reasons. In cases where relatively few components have been tested to failure a statistically significant number of times (e.g., when components are designed for high reliability), then there may be relatively few failures that have been recorded. However, even in such cases, it still may be possible to amass a large library of healthy component data that may be used to establish nominal CI thresholds based, for example, on a desired small false alarm rate. Note that establishing a threshold based on a relatively small false alarm rate has advantages. For example, if the false alarm rate is low, an operator may be assured that a component that has exceeded a threshold has failed. However, establishing such a threshold can only be done if the underlying distribution of the CI is correct.

According to an embodiment of the system described herein, a Rayleigh distribution may be used to model shaft vibration when the shaft is healthy. Shaft order one (SO1) is the vibration energy at one times the shaft RPM, and may be associated with an out of balance condition. Shaft order two (SO2), the vibration energy at two times the shaft RPM, may be associated with shaft bending. Shaft order three (SO3), the vibration energy at three times the shaft RPM, may be an indicator of a broken flange. Note that it is possible for the aircraft manufacturer to have set limits to indicate when maintenance is required. In some cases, test stand data or seeded fault tests may be used to gain insight into an appropriate threshold for maintenance. However, for some components, thresholds may be set statistically. That is, CIs for a component may be calculated over a number of flight regimes, and for a number of aircraft. The CIs form a distribution for nominal aircraft, and a threshold may be set, for example, at a nominal probability of false alarm (PFA) of $10^{-6}$, estimated variance/mean values and/or the inverse cumulative distribution.

Figure 4:
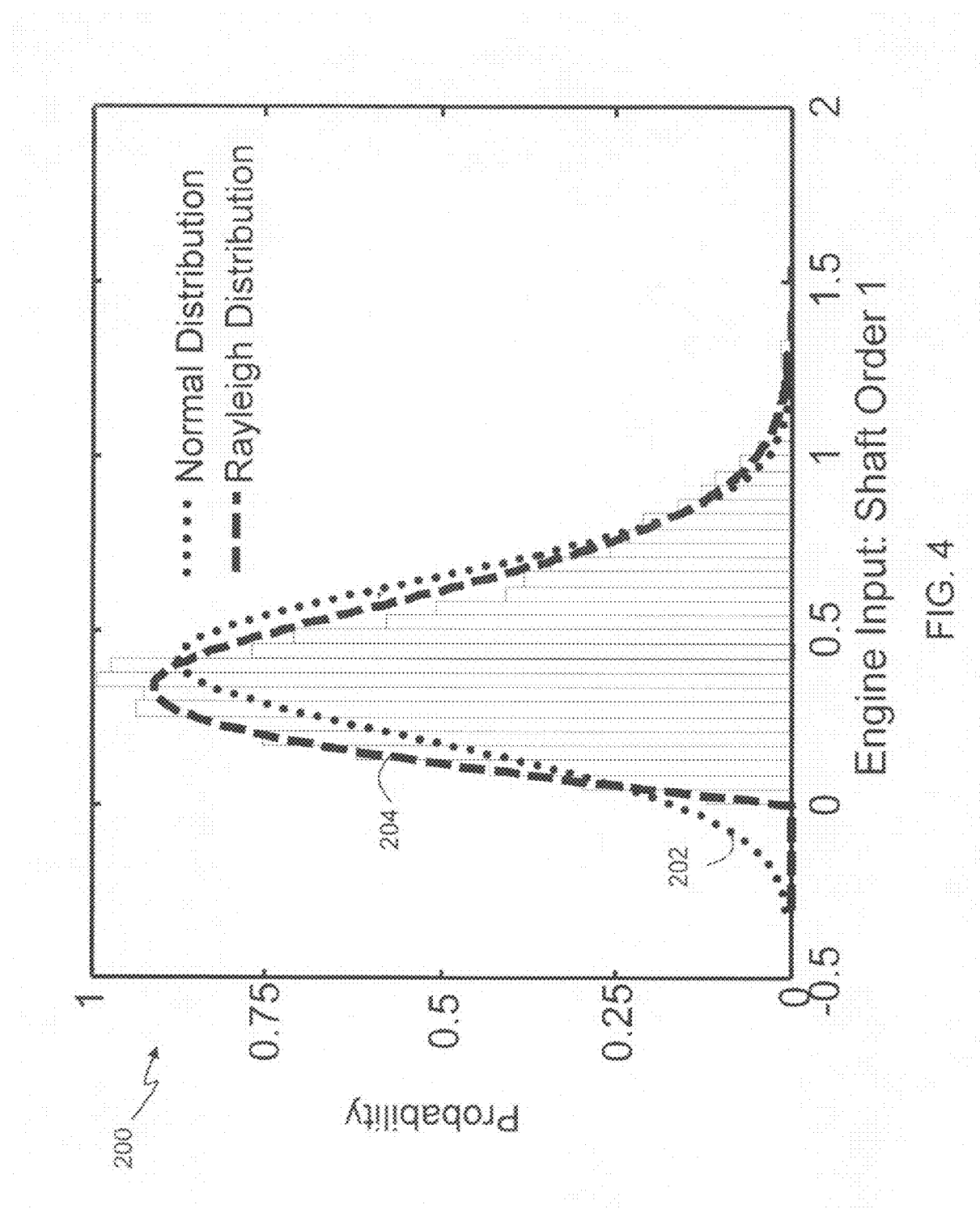
FIG. 4 illustrates various probabilities and distribution functions for specific values of measured vibration energy corresponding to engine input shaft order one.

FIG. 4 is a schematic diagram 200 that illustrates various probabilities for specific values for measured vibration energy corresponding to engine input shaft order one. The vertical axis represents probability while the horizontal axis represents specific values for vibration energy. The diagram 200 includes a plurality of histograms drawn vertically from the horizontal axis. The histograms may represent the number of times the actual measured vibration energy at shaft, order one equals the corresponding value on the horizontal axis when the shaft is healthy. The histogram values are converted to the probability values of the vertical axis by normalizing the histogram values according to the total number of samples.

The diagram 200 also includes a first graph 202 showing a normal (Gaussian) distribution and a second graph 204 showing a Rayleigh distribution. The graphs 202, 204 are superimposed on to the CI probability histograms and are meant to approximate healthy component distributions. Note that the second graph 204 appears to model the histogram/probability data more closely, in part because the second graph 204 contemplates only positive values for vibration energy while the first graph 202 appears to include probabilities for some negative energy values, which of course do not occur under real-world conditions Assuming that the distribution of healthy component vibration energy data is a Rayleigh distribution, then the probability of vibration energy being measured as M or less when a component is healthy is given by the equation:

$$F(M) = 1 - \exp(-M^2/2\sigma^2)$$

where $\sigma$ is the standard deviation of the measured data and thus $\sigma^2$ is the variance. Note that the standard deviation may be determined empirically by applying known techniques to a plurality of measured vibration values taken when the component is healthy. For the Rayleigh distribution, the underlying standard deviation is a function of either the measured mean or the measured variance. If calculated from the mean value, s=mean/sqrt(pi/2). If from variance, the underlying standard deviation is: s=sqrt(var/(2−pi/2)). For example, the standard deviation may be calculated from data like the data shown in the graph 200 using the formula:

$$\sigma^2 = \frac{\sum (\text{measured\_value} - \text{mean})^2}{\text{number\_of\_data\_pnts}}$$

Given the equation F(M), it is possible to set a threshold for expected false alarm rate and then solve for M to obtain a threshold value. For example, suppose the desired false alarm rate is 1% so that F(M) equals 0.01, thus:

$$0.01 = 1 - \exp(-M^2/2\sigma^2)$$

$$0.99 = \exp(-M^2/2\sigma^2)$$

$$\ln(0.99) = (-M^2/2\sigma^2)$$

$$M = \sqrt{2\sigma^2 * \ln(1/0.99)}$$

It is possible to extend setting thresholds for specific CI's to apply to any generalized probability distribution (e.g. non-Gaussian distribution) and any health indicator (HI) algorithm to allow setting a probability of false alarm (PFA) for a component taking into account the interaction of n number of condition indicators (CI's).

Generally, the Rayleigh distribution may be used in instances where the distribution is a function of the magnitude of two Gaussian distribution. There are a number of values other than shaft vibrations where this may be applicable, such as bearing vibration data. It is also possible to extend the techniques described herein to take into account the covariance of related, but different, CI's. For example, in the case of CI's associated with different orders of shaft vibration data, generally when vibrations associated with one shaft order increase, then vibrations associated with other shaft orders may also increase.

In some cases, when a shaft (or similar component) becomes faulted, the measured shaft orders may no longer be zero. The Rayleigh distribution, as noted, assumes that the underlying Gaussian distribution has a zero mean. As such, it may be useful to assume a different model for a damaged component. This different model may be used for analysis once measured values have exceeded the thresholds set according to use of the Rayleigh distribution on data corresponding to healthy components as discussed elsewhere herein.

Transmission error (TE) may depend upon torque. TE is a cause of vibration, while the intensity of the vibration is a function of the frequency response ($N_r$), where frequency is a function of RPM. Consider, for example, a deflection in a spring that is linearly related to the force applied to the spring. The transmissions discussed herein may be similar in certain aspects to a large, complex spring. That is, the displacement of a pinion and its corresponding TE is proportional to the torque applied. Thus, vibration and the corresponding CI calculated using data acquisition may be approximately linearly proportional to torque, Nr (over the operating range of interest) and/or airspeed although at times there may be a linear torque*Nr interaction effect. It should be noted that test data, for example used in connection with a Bell helicopter H-1 loss of lube test, shows a relationship between CI and torque suggesting linearity. Other embodiments of the system described herein may take into account any one or more of the above-noted factors as well as apply the techniques described herein to other factors that may be relevant in a particular embodiment or other application. Specifically, according to the system described herein, and as further discussed in more detail elsewhere herein, determining trending of vibration data in connection with predicting component health at future points in time may be enhanced and/or otherwise facilitated by taking into account the effect of torque.

In shaft analysis using vibration based mechanical diagnostics based on CIs, as further discussed elsewhere herein, acceleration associated with the first (SO1), second (SO2) and third (SO3) harmonic of the shaft revolution is indicative of various faults. SO1 is indicative of an imbalance or slightly damaged shaft, SO2 is present with a bent shaft, and SO3 alone, or with SO2, may indicate a shaft coupling failure. The measured CI may be a function of transmission error (TE) and, for example, some part of the transmitted power in a shaft with an imbalance drives the SO1 acceleration. Because there exists a relationship between TE and the CI (the TE, in effect, causes a change in the CI) for a component that is faulted, the CI is correlated with power transmitted.

In drive train components, power may be proportional to measured torque. In terms of diagnostics or trending of a component, it may be desirable to reduce the scatter in the measured CI and account for this torque. While the relationship between torque and the CI can be seen by plotting torque versus CI, from a diagnostics perspective, it is preferable to capture this relationship in time. Time/trend plots capture the time or progression of a fault. An increase in the correlation of torque with the CI would indicate an increase of TE, which indicates the propagation of a fault.

Figure 5:
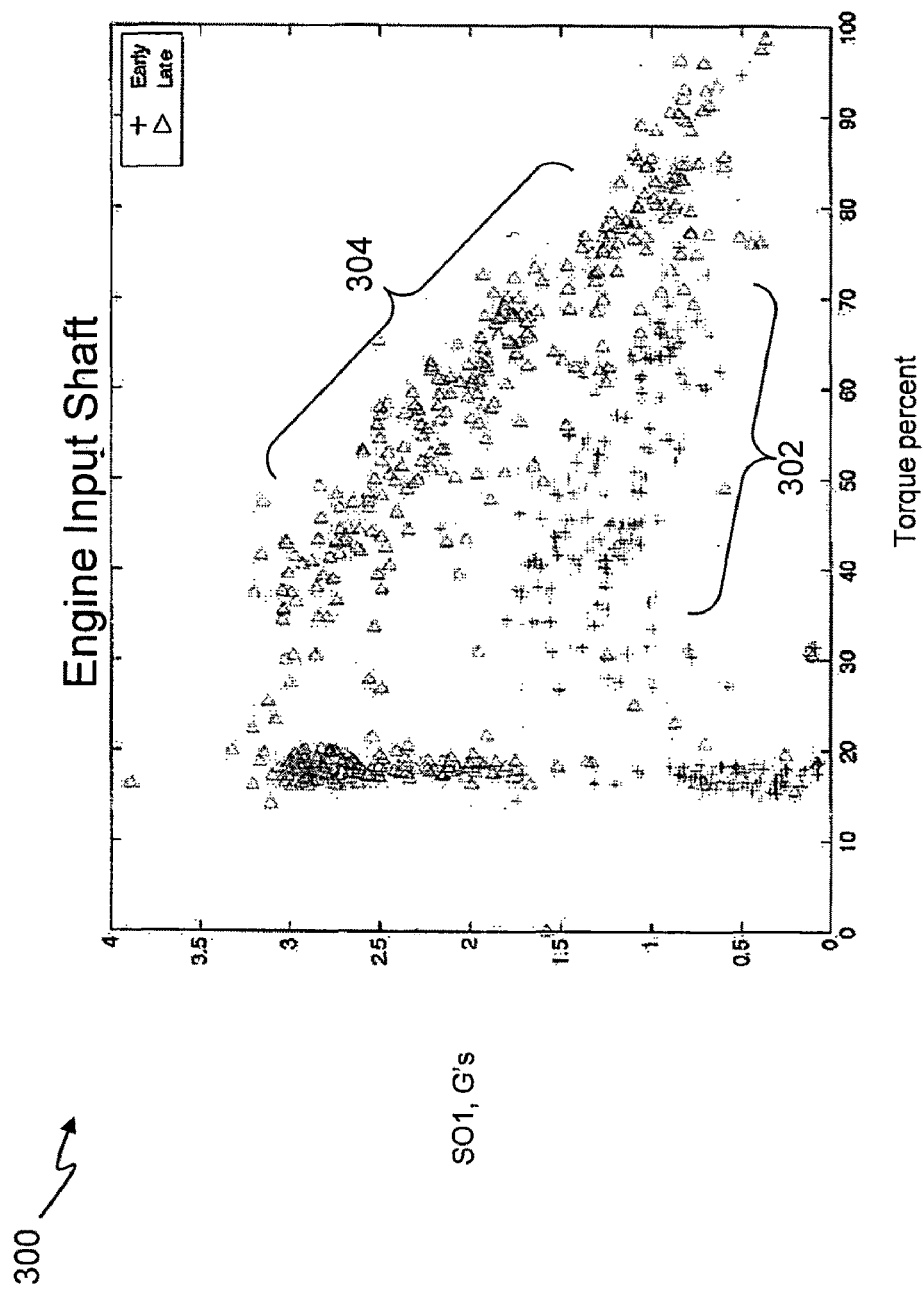
FIG. 5 is a plot showing a relationship between the CI and torque over two time periods for an engine input shaft according to an embodiment of the system described herein.

FIG. 5 is a plot 300 showing a relationship between the CI (e.g., SO1, G-level along the vertical axis) and torque over two time periods for an engine input shaft according to an embodiment of the system described herein. The two time periods are identified as "early" data (shown approximately around region 302) and "late" data (shown approximately around region 304) with torque being shown in percent along the horizontal access. As illustrated, the relationship between the CI and the torque (slope) changes between the early data 302 compared to that of the late data 304 due to a propagating fault. Accordingly, the system described herein provides a methodology to estimate the effect of torque on the CI dynamically over time. The system described herein provides a reduction in CI variance and gives insight into the condition of the component by observing when the effect of the torque is statistically significant, which is indicative of a propagating fault.

A relatively simple model for the CI/torque relationship may be written as:

$$CI_{Measured} = CI + B*\text{torque} \qquad \text{[Equation 1]}$$

where B is the torque coefficient. As further discussed elsewhere herein, the actual CI (e.g., SO1) may be affected by torque in a linear manner, and the above-noted linear model may be generally used on that basis. Other models for the CI/torque relationship may also be used in connection with the system described herein and may depend, for example, on the CI and the type of component being analyzed. For example, the system described herein may be applied to non-linear relationships between a CI and torque, such as a quadratic relationship, and appropriate models used accordingly.

In a batch process mode, the linear relationship of Equation 1 may be estimated by linear regression:

$$B = \text{inv}(H'*H)*H'*CI \qquad \text{[Equation 2]}$$

where H is a matrix of [1 trq(i)]. However, since this methodology does not capture the time evolution process of component degradation, it may not be sufficient to identify the trending effect of torque. Because the effect of torque is effectively "hidden" in the measurement, a state observer may be used to reconstruct the hidden state. State observers that may be used in connection with the system described herein may include a recursive least squares estimator, a Particle filter, a Kalman filter and/or other suitable state observer, including for example, an extended Kalman filter or an unscented Kalman filter.

Figure 6:
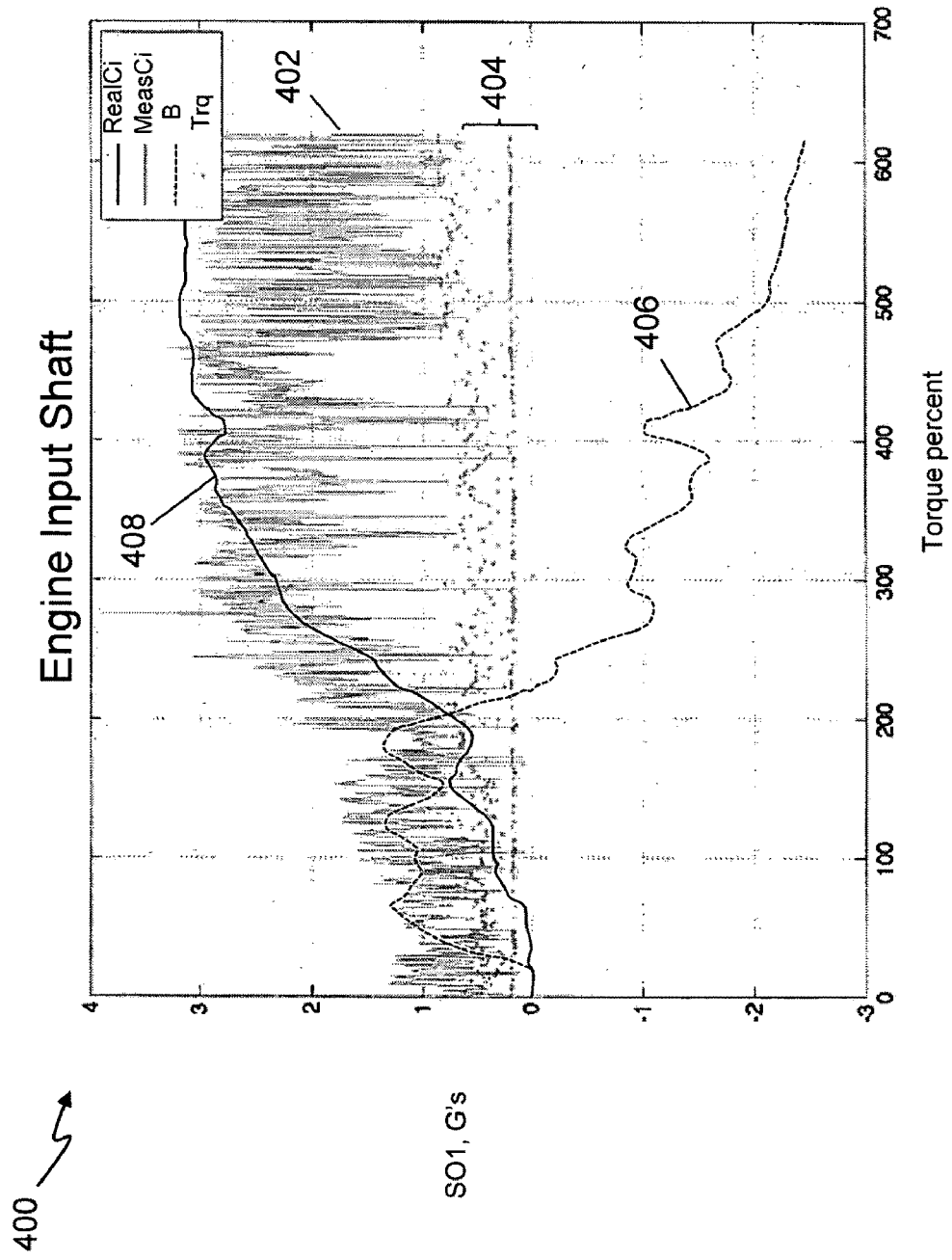
FIG. 6 is a plot showing application of a recursive least squares estimator that captures the correlation in the relationship over time between torque and CI that is seen in FIG. 5.

FIG. 6 is a plot 400 showing application of a recursive least squares estimator that captures the correlation in the relationship over time between torque and CI that is seen in FIG. 5 according to an embodiment of the system described herein. FIG. 6 shows the measured CI 402, the torque 404, B (torque coefficient) values 406, and the real CI 408 after filtering according to recursive least squares estimation. In a recursive least squares estimation, regression may be performed on a window of data k units long:

$$z^k = \begin{bmatrix} z(i-k) \\ \vdots \\ z(i) \end{bmatrix},$$

$$H^k = \begin{bmatrix} H(i-k) \\ \vdots \\ H(i) \end{bmatrix}$$

where z is the measured CI, H is the measurement matrix (e.g., appropriate torque values applied) and the recursive algorithm is:

$$P = \sigma^2 (H^T H)^{-1}$$

$$W = PH^T$$

$$Y_i = Y_{i-1} + W(z - Hy_{i-1}) \qquad \text{[Equations 3a, 3b, 3c]}$$

The above-noted least squares estimation is powerful but computationally complex, requiring the inversion of a matrix, and also the window reduces the system response to changes in the monitored system, as seen in FIG. 6 (shown for k=20).

Figure 7:
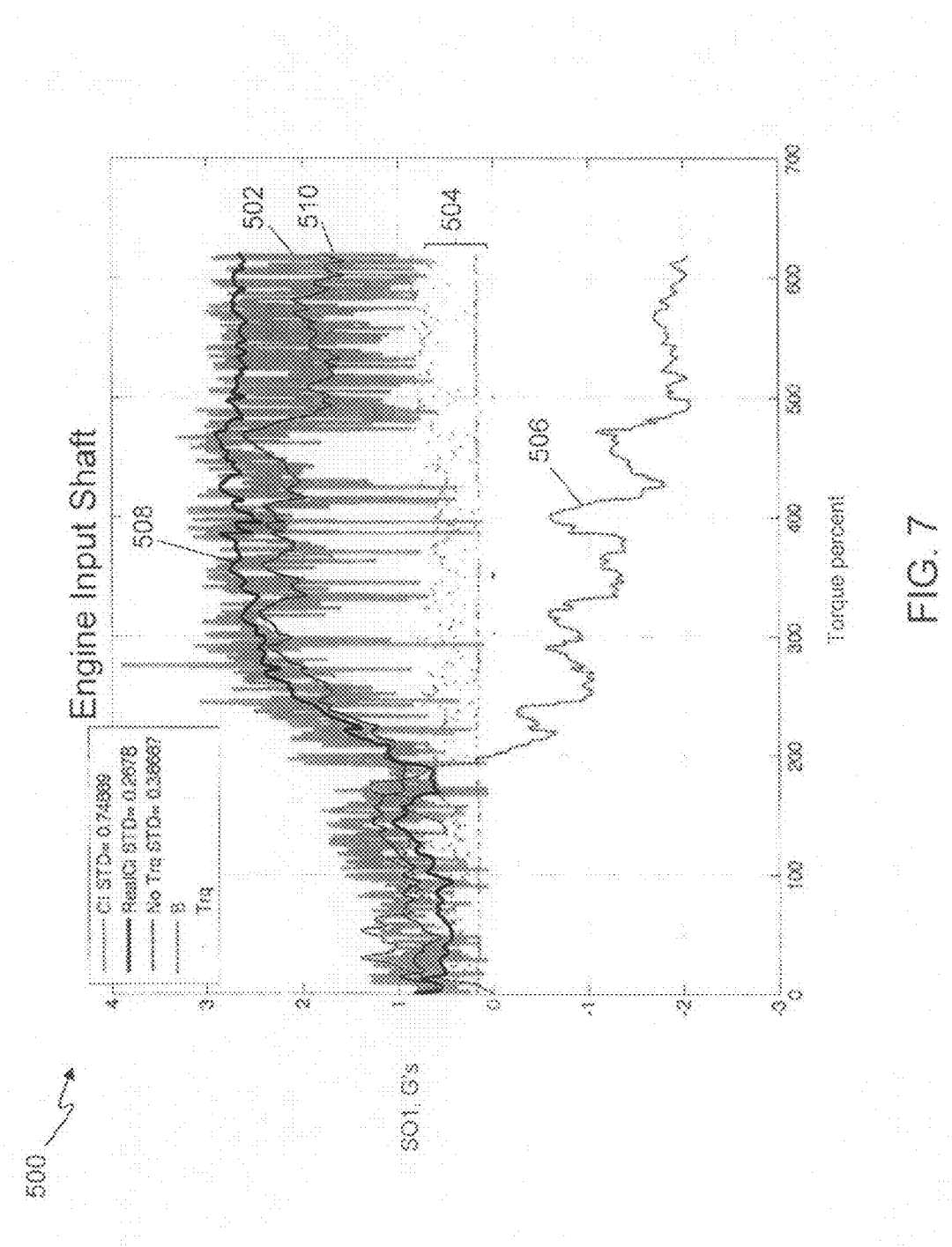
FIG. 7 is a plot showing a Kalman filter implementation of the data of FIG. 5 according to an embodiment of the system described herein.

FIG. 7 is a plot 500 showing a Kalman filter implementation of the data of FIG. 5 according to an embodiment of the system described herein. A Kalman filter is a recursive algorithm that optimally filters the measured state based on a priori information such as the measurement noise, the unknown behavior of the tracked state, and the time between measurements. The plot 500 shows measured CI 502, the torque 504, the estimated effect of torque (B) 506, the Kalman filtered CI 508, and the same Kalman filtered CI without any torque model 510. Values are also shown for the standard deviations of the measured CI (Ci), Kalman filtered CI (RealCi) and filtered CI without any torque model (No Trq). Note that without accounting for the effect of torque, the filter CI 510 is the mean value of the noise. The Kalman filter may be used for various reasons due to the particular factors taken into account in the embodiment and uses described herein, in particular, taking into account the noise of a particular arrangement of components. It should be noted that other systems embodying concepts and techniques described herein may also take into account other noise factors.

Computationally, the use of the Kalman filter does not require a matrix inversion and the Kalman filter algorithm is a one-step iterative process (i.e., only the last state information is required versus the last k data points as per the recursive least squares estimation). In the model illustrated by FIG. 7, a four state Kalman filter is designed to track: the real (hidden) CI; dCI/dt (the rate of change of the CI); B (the hidden effect of torque (torque coefficient)); and dB/dt (the rate of change of the torque coefficient).

The measurement matrix, H, is [1 0 torque(t) 0], whereas the transition matrix (F) is:

$$F = \begin{bmatrix} 1 & t & 0 & 0 \\ 0 & 1 & 0 & 0 \\ 0 & 0 & 1 & t \\ 0 & 0 & 0 & 1 \end{bmatrix}$$

and the system noise (unknown behavior of the tracked state) is modeled as a white noise process according to the following Q matrix:

$$Q = \begin{bmatrix} \frac{1}{4}t^4 & \frac{1}{2}t^3 & 0 & 0 \\ \frac{1}{2}t^3 & t^2 & 0 & 0 \\ 0 & 0 & \frac{1}{4}t^4 & \frac{1}{2}t^3 \\ 0 & 0 & \frac{1}{2}t^3 & t^2 \end{bmatrix}$$

The recursive state estimator algorithm is then:

$X_{t|t-1} = FX_{t-1|t-1}$ $z = HX_{t|t-1}$ $P_{t|t-1} = FP_{t-1|t-1}F^T + Q$ $S = HP_{t-1|t-1}H^T + R$ $W = P_{t|t-1}H^T(S)^{-1}$ $X_{t|t} = X_{t|t-1} - W(ci-z)$ $P_{t|t} = P_{t|t-1} - WSW^T$ [Equations 4a-4g]

By taking into account torque, which would normally inject noise randomly into the measured CI, the filter CI may show a measurable reduction in variance (see FIG. 7).

Figure 8:
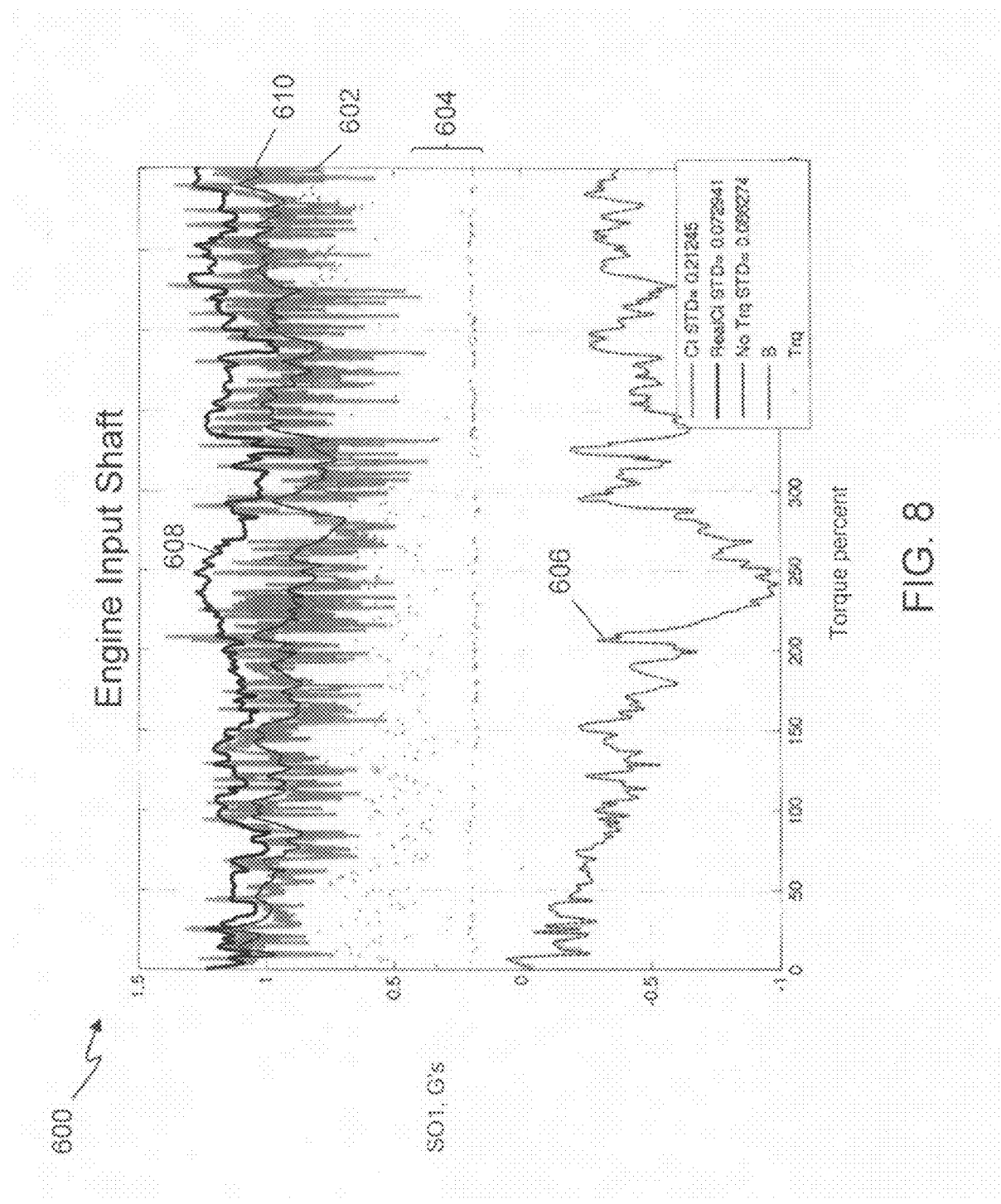
FIG. 8 is a plot showing the measured CI, the torque, the estimated effect of torque (B), the filtered CI, and the same filtered CI without any torque model, and specifically illustrating a negative torque/CI relationship in an engine input shaft according to an embodiment of the system described herein.

FIG. 8 is a plot 600 showing the measured CI 602, the torque 604, the estimated effect of torque (B) 606, the filtered CI 608, and the same filtered CI without any torque model 610, and specifically illustrating a negative torque/CI relationship in an engine input shaft according to an embodiment of the system described herein. Values for the standard deviations of the measured CI (Ci), filtered CI (RealCi) and filtered CI without any torque model (No Trq) are also shown. Note that without accounting for the effect of torque, the resulting filter CI 610 is the mean value of the noise. Also note that there is a 20% reduction in the standard deviation. The negative torque/CI relationship that is illustrated may occur when there is misalignment between components (as torque increases, TE is reduced), but may not be indicative of a propagating fault. Low G levels are seen in the graph (up to 1.5 G) (for example, for the tested component, failure would expected at 10+ G's).

Figure 9:
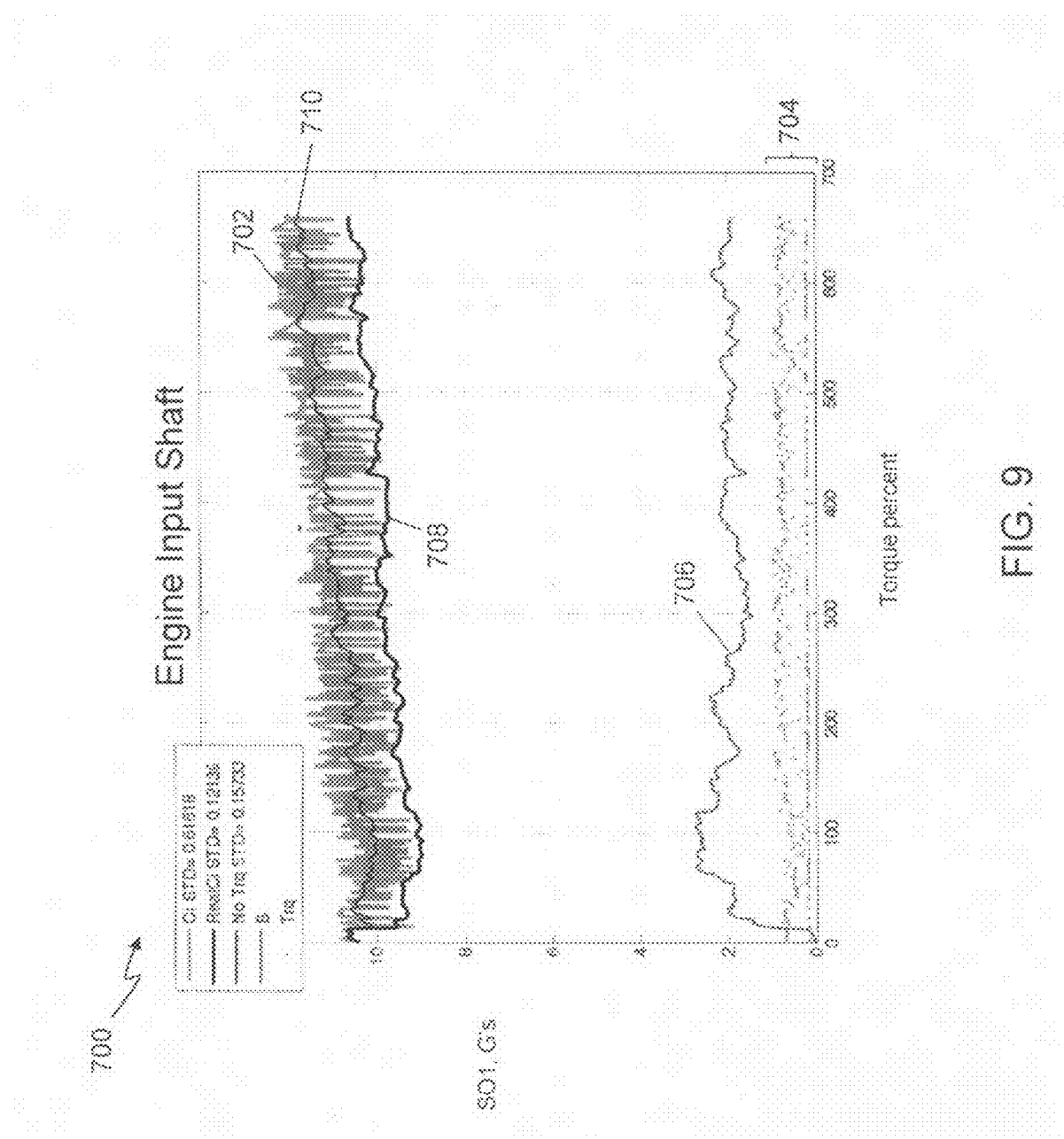
FIG. 9 is a plot showing a positive torque relationship that is indicative of fault propagation in an engine input shaft according to an embodiment of the system described herein.

FIG. 9 is a plot 700 showing a positive torque relationship that is indicative of fault propagation in an engine input shaft according to an embodiment of the system described herein. Shown are the measured CI 702, the torque 704, the estimated effect of torque (B) 706, the filtered CI 708, and the same filtered CI without any torque model 710. The component is faulted and the high G level (around 10) may be noted. The torque effect may be noted as 2G's*percent torque (the horizontal axis measure). Specifically, for example, 100% torque causes the measured CI to jump 2 G's. The torque effect may account for a large amount of the scatter of the data.

Figure 10:
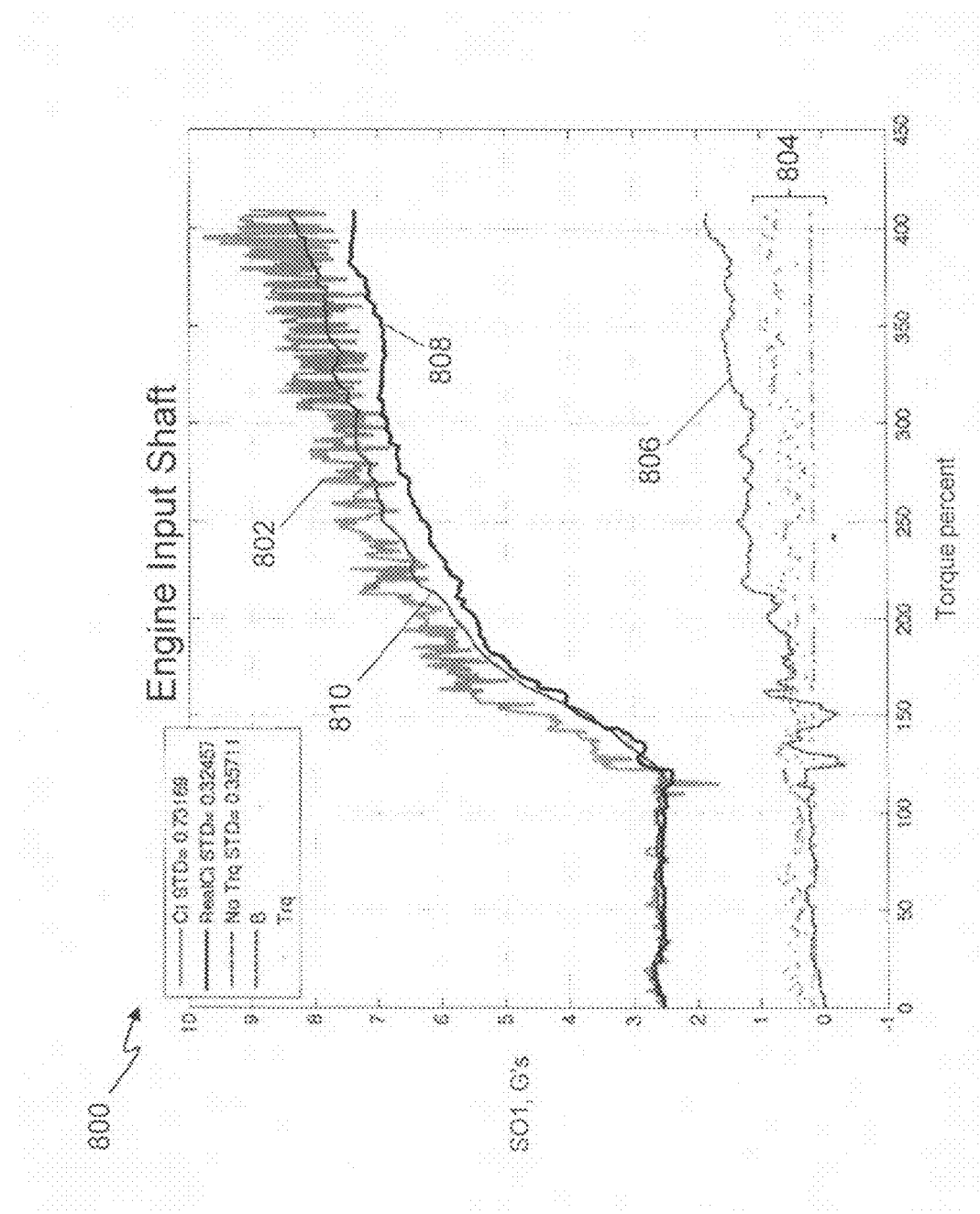
FIG. 10 is a plot showing an increasing positive torque relationship coinciding with fault propagation in an engine input shaft according to an embodiment of the system described herein.

FIG. 10 is a plot 800 showing an increasing positive torque relationship coinciding with fault propagation in an engine input shaft according to an embodiment of the system described herein. Shown are the measured CI 802, the torque 804, the estimated effect of torque (B) 806, the filtered CI 808, and the same filtered CI without any torque model 810. The figure shows the results from a known fault for a component, determined upon inspection to be a fretted spline coupling. It may be noted that there is, effectively, no torque effect until the torque is at 120% where it is observed that the fault starts to propagate.

Figure 11:
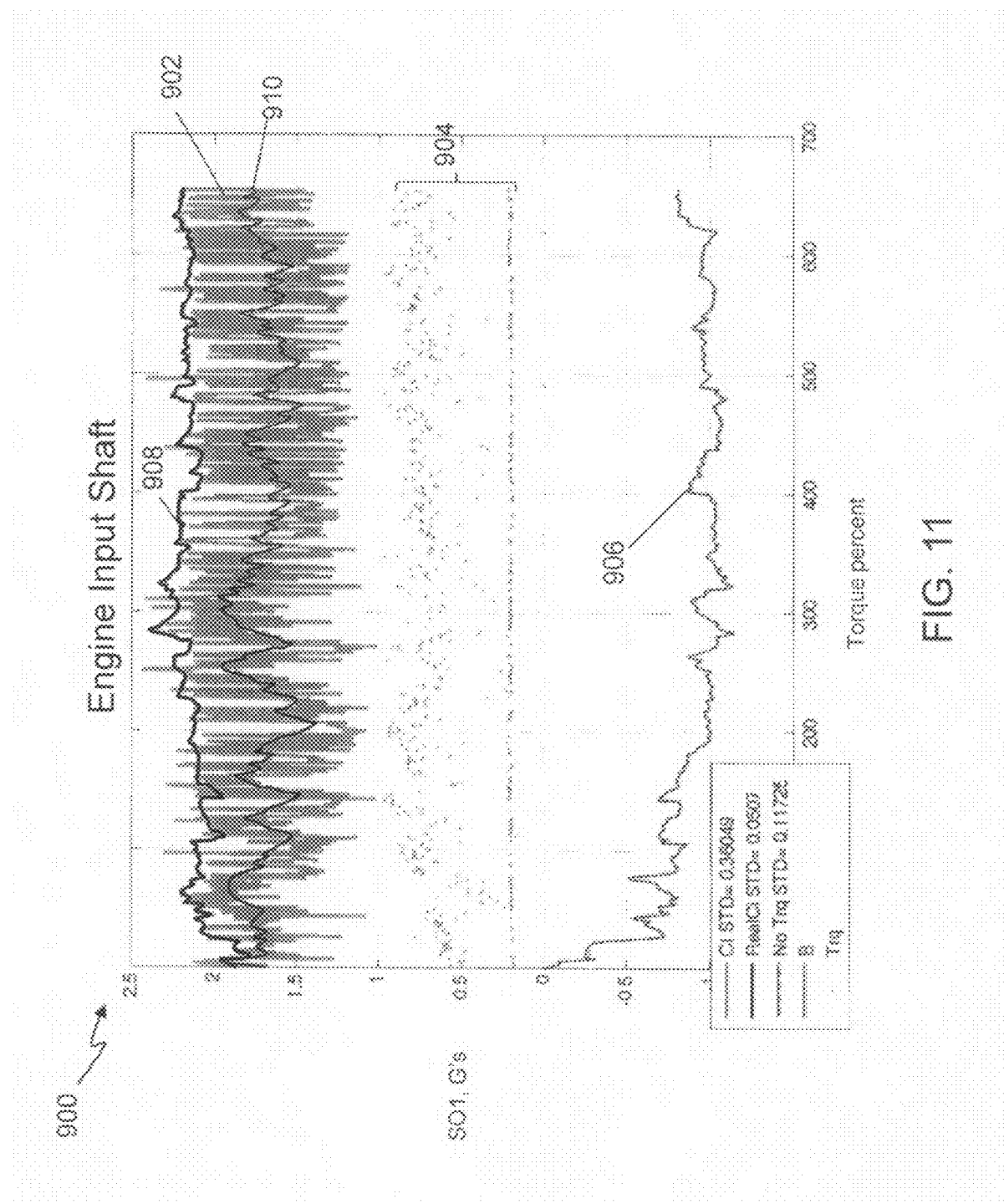
FIG. 11 is a plot showing scatter reduction achieved by taking into account torque in an engine input shaft according to an embodiment of the system described herein.

FIG. 11 is a plot 900 showing scatter reduction achieved by taking into account torque in an engine input shaft according to an embodiment of the system described herein. Shown are the measured CI 902, the torque 904, the estimated effect of torque (B) 906, the filtered CI 908, and the same filtered CI without any torque model 910. The figure shows a measurable torque effect on the engine input shaft. In this case, the gear involutes may be cut such that the TE is lowest when under 100% torque. Here, the observed negative torque relationship reflects this gear shaft manufacturing process and again reduces scatter in the measured data.

Figure 12:
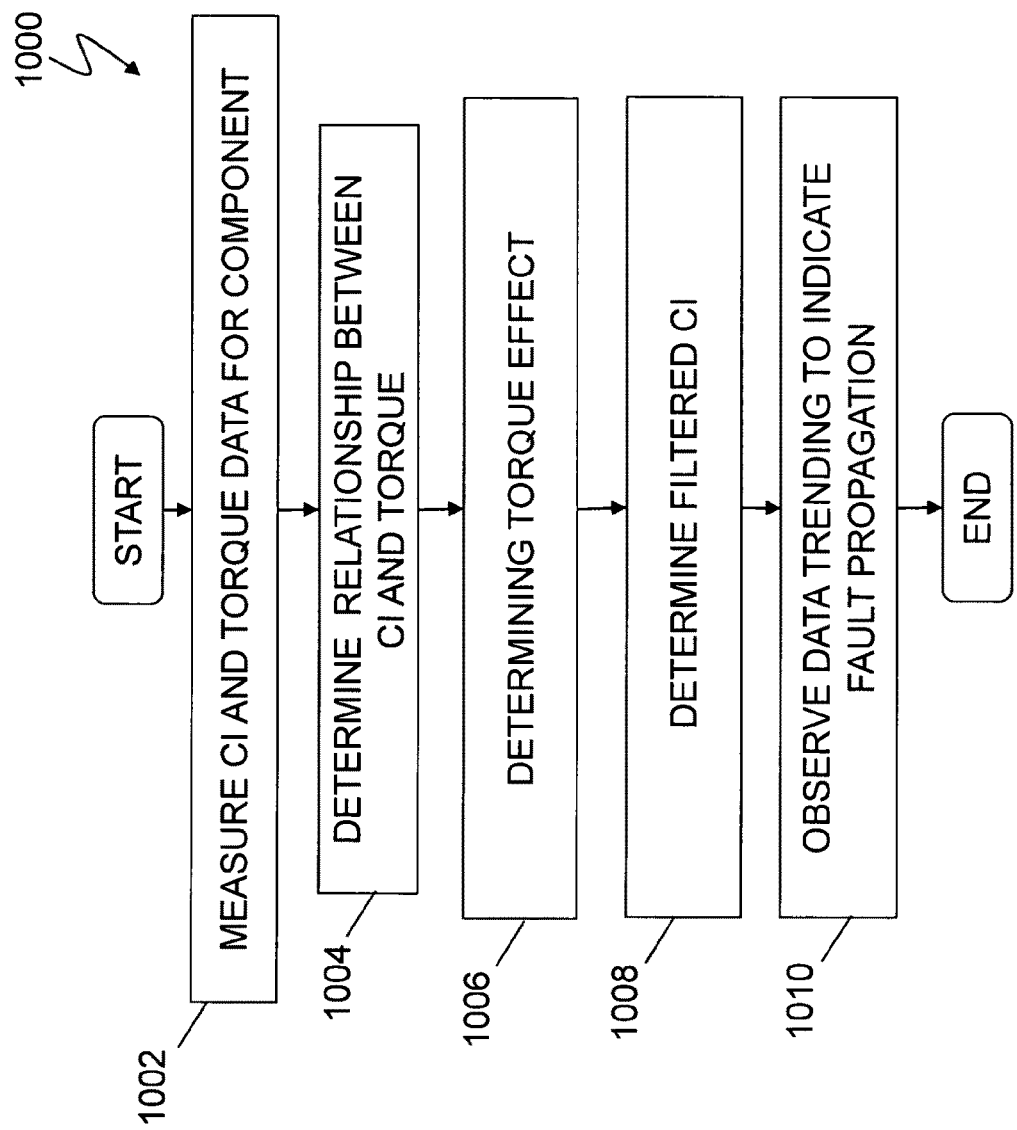
FIG. 12 is a flow chart showing steps for determining the torque effect on a CI for a component and the use thereof in indicating fault propagation according to an embodiment of the system described herein.

FIG. 12 is a flow chart 1000 showing steps for determining the torque effect on a CI for a component and the use thereof in indicating fault propagation according to an embodiment of the system described herein. At a step 1002, data is measured for the component. The measured data may included data for a selected CI of the component along with measured data for torque. After the step 1002, processing proceeds to a step 1004 where a relationship is determined between the CI and torque, for example, according to a linear relationship as further discussed elsewhere herein. After the step 1004, processing proceeds to a step 1006 where the effect of torque is determined using a filtering technique, such as a Kalman filter and/or recursive least squares estimator, as further discussed elsewhere herein. After the step 1006, processing proceeds to a step 1008 where the filtered (actual) CI is determined based on the use of the filtering technique. As further discussed elsewhere herein, a large amount of the scatter of the measured CI data may based on the effect of torque and may therefore be eliminated by accounting for the torque effect. After the step 1008, processing proceeds to a step 1010 where the observed trending of the filtered CI data over time in correlation with the torque measurements may be used to indicate whether a fault is propagating in the component. Specifically, as further discussed elsewhere herein, the effect of torque being statistically significant in connection with the observed trending of the filtered CI is indicative of a propagating fault. After the step 1010, processing is complete.

It may be noted that the techniques of the system described herein may be applied to input factors, other than torque, that may affect the measured CI. For example, in the case of the tail rotor, SO1 may be correlated to foot pedal position and/or airspeed in connection with appropriate models for the effects of these other input factors. An additional state may be added to reconstruct the "hidden" parametric effect. Accordingly, the devices and techniques disclosed herein, for example the steps shown and described in connection with FIG. 12, may also be applied in connection with the other effects.

Various embodiments discussed herein may be combined with each other in appropriate combinations in connection with the system described herein. Additionally, in some instances, the order of steps in the flow charts or flow diagrams may be modified, where appropriate. Further, various aspects of the system described herein may be implemented using software, hardware, and/or a combination of software and hardware. Software implementations of the system described herein may include executable code that is stored in a computer readable storage medium and executed by one or more processors. The computer readable storage medium may include a computer hard drive, ROM, RAM, flash memory, portable computer storage media such as a CD-ROM, a DVD-ROM, a flash drive and/or other drive with, for example, a universal serial bus (USB) interface, and/or any other appropriate tangible storage medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method of indicating a propagating fault in a component, comprising:
  measuring data corresponding to a condition indicator of the component and to an input factor, wherein the condition indicator of the component includes a vibration measure and the input factor is torque;
  determining, using at least one processor, a relationship between the condition indicator and the input factor;
  determining, using at least one processor, an effect of the input factor on the condition indicator;
  determining, using at least one processor, a filtered condition indicator based on the effect of the input factor on the condition indicator; and
  determining, using at least one processor, whether a propagating fault is indicated based on a correlation over a time period of the filtered condition indicator with the input factor, wherein the propagating fault is indicated according to the correlation over the time period of the filtered condition indicator with the torque input factor where the effect of the torque input factor on the condition indicator is determined as statistically significant in connection with trending of the filtered condition indicator over the time period.

2. The method according to claim 1, wherein determining the effect of the input factor on the condition indicator includes using a state observer.

3. The method according to claim 2, wherein the state observer is at least one of: a Kalman filter, a recursive least squares estimation, and a Particle filter.

4. The method according to claim 1, wherein the component is a rotating shaft.

5. The method according to claim 1, wherein data of the filtered condition indicator has a reduced variance compared to the data measured corresponding to the condition indicator.

6. The method according to claim 1, wherein the propagating fault is determined based on a positive correlation over time between the filtered condition indicator and the input factor.

7. A non-transitory computer readable storage medium storing computer software that determines indication of a propagating fault in a component, the computer software comprising:
  executable code that measures data corresponding to a condition indicator of the component and to an input factor, wherein the condition indicator of the component includes a vibration measure and the input factor is torque;
  executable code that determines a relationship between the condition indicator and the input factor;
  executable code that determines an effect of the input factor on the condition indicator;
  executable code that determines a filtered condition indicator based on the effect of the input factor on the condition indicator; and
  executable code that determines whether a propagating fault is indicated based on a correlation over time of the filtered condition indicator with the input factor, wherein the propagating fault is indicated according to the correlation over the time period of the filtered condition indicator with the torque input factor where the effect of the torque input factor on the condition indicator is determined as statistically significant in connection with trending of the filtered condition indicator over the time period.

8. The non-transitory computer readable storage medium according to claim 7, wherein the executable code that determines the effect of the input factor includes executable code that uses a state observer.

9. The non-transitory computer readable storage medium according to claim 8, wherein the state observer includes at least one of: a Kalman filter, a recursive least squares estimation, and a Particle filter.

10. The non-transitory computer readable storage medium according to claim 7, wherein the component is a rotating shaft.

11. The non-transitory computer readable storage medium according to claim 7, wherein data of the filtered condition indicator has a reduced variance compared to the data measured corresponding to the condition indicator.

12. The non-transitory computer readable storage medium according to claim 7, wherein the propagating fault is determined based on a positive correlation over time between the filtered condition indicator and the input factor.

13. A system for indicating a propagating fault in a component, comprising:
  a first sensor that measures data corresponding to a condition indicator of the component, wherein the condition indicator of the component includes a vibration measure; and
  a second sensor that measures data corresponding to an input factor, wherein the input factor is torque; and
  at least one processor that processes the data measured from the first sensor and the second sensor, the at least one processor executing computer software stored on a computer readable storage medium, the computer software comprising:
    executable code that determines a relationship between the condition indicator and the input factor;
    executable code that determines an effect of the input factor on the condition indicator;
    executable code that determines a filtered condition indicator based on the effect of the input factor on the condition indicator; and
    executable code that determines whether a propagating fault is indicated based on a correlation over time of the filtered condition indicator with the input factor, wherein the propagating fault is indicated according to the correlation over the time period of the filtered condition indicator with the torque input factor where the effect of the torque input factor on the condition indicator is determined as statistically significant in connection with trending of the filtered condition indicator over the time period.

14. The system according to claim 13, wherein the executable code that determines the effect of the input factor includes executable code that uses a state observer.

15. The system according to claim 14, wherein the state observer includes at least one of: a Kalman filter, a recursive least squares estimation, and a Particle filter.

16. The system according to claim 13, wherein data of the filtered condition indicator has a reduced variance compared to the data measured corresponding to the condition indicator.

17. The system according to claim 13, wherein the propagating fault is determined based on a positive correlation over time between the filtered condition indicator and the input factor.

* * * * *